United States Patent [19]

Pahade

[11] Patent Number: 4,501,600
[45] Date of Patent: Feb. 26, 1985

[54] PROCESS TO SEPARATE NITROGEN FROM NATURAL GAS

[75] Inventor: Ravindra F. Pahade, North Tonawanda, N.Y.

[73] Assignee: Union Carbide Corporation, Danbury, Conn.

[21] Appl. No.: 514,338

[22] Filed: Jul. 15, 1983

[51] Int. Cl.³ .................................................. F25J 3/02
[52] U.S. Cl. ........................................... 62/28; 62/31; 62/33; 62/34; 62/40
[58] Field of Search ............................ 62/9, 11, 23-34, 62/38, 39, 40

[56] References Cited

U.S. PATENT DOCUMENTS

| | | | |
|---|---|---|---|
| 3,443,388 | 5/1969 | Kramer et al. | 62/28 |
| 3,531,943 | 10/1970 | Parnag et al. | 62/28 |
| 3,818,714 | 6/1974 | Etzbach et al. | 62/11 |
| 4,352,685 | 10/1982 | Swallow | 62/28 |
| 4,411,677 | 10/1983 | Pervier et al. | 62/25 |
| 4,415,345 | 11/1983 | Swallow | 62/28 |

OTHER PUBLICATIONS

Crawford et al., Design and Operating Characteristics of the Sunflower Helium Plant, Journal Petroleum Technology, Sep. 1970, pp. 1098–1102.
Chiu, Exergy Analysis Aids Equipment Design for Cryogenic Process, Oil and Gas Journal, Jan. 18, 1982, pp. 88–91.

Primary Examiner—Frank Sever
Attorney, Agent, or Firm—Stanley Ktorides

[57] ABSTRACT

A cryogenic process to more efficiently separate nitrogen from a nitrogen-containing hydrocarbon stream wherein the separate recovery of natural gas liquids is increased and the final nitrogen removal from natural gas is accomplished at lower than conventional pressures. The nitrogen-methane separation column is driven by a closed loop heat pump circuit that utilizes a nitrogen-methane mixture.

13 Claims, 1 Drawing Figure

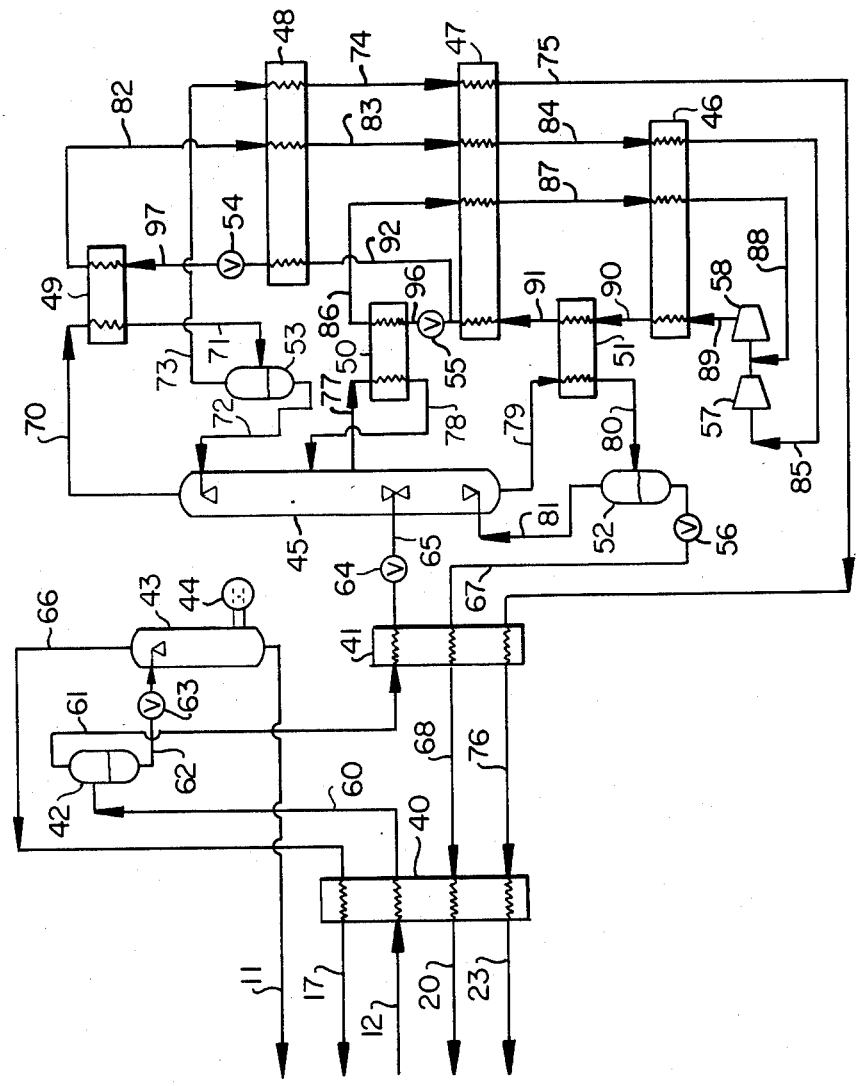

PROCESS TO SEPARATE NITROGEN FROM NATURAL GAS

TECHNICAL FIELD

This invention relates to the separation of nitrogen from natural gases and is particularly applicable for use to separate a stream from a well into methane, natural gas liquids, and nitrogen.

BACKGROUND ART

As hydrocarbon resources become scarcer and more difficult to recover, secondary recovery operations are becoming more widespread. Such secondary recovery operations are commonly referred to as enhanced oil recovery (EOR) and enhanced gas recovery (EGR) operations. One such secondary recovery technique involves the injection of a gas which does not support combustion into a reservoir to raise reservoir pressure in order to remove hydrocarbons which cannot be removed from the reservoir by natural reservoir pressure. A commonly used gas for this process is nitrogen because it is relatively abundant and inexpensive and can be produced in large quantities at the reservoir site.

Over time, nitrogen injected at the reservoir will begin to be removed with the hydrocarbons. This requires the removal of the nitrogen from the hydrocarbon stream in order to satisfy minimum heat content requirements or maximum inert content requirements of the product fuel gas.

Conventional processes for removing nitrogen from natural gases, often termed nitrogen rejection processes, separate the reservoir stream into methane, nitrogen, and hydrocarbons having two or more carbon atoms which are often termed natural gas liquids. Conventional processes effect this separation by first separating the reservoir stream into a liquid stream containing primarily natural gas liquids and into a vapor stream containing primarily nitrogen and methane. The liquid stream is recovered and the vapor stream is separated cryogenically in one or more rectification columns into nitrogen and methane. When a single rectification column is used to make the cryogenic rectification, the column is often driven by a recirculating fluid heat pump. The fluid for this heat pump is generally methane since it can match the reboiler and condenser temperatures required with reasonable pressure levels.

One problem with such conventional processes is that some of the natural gas liquids are not separated out in the first separation but instead remain with and are recovered with the methane. This is disadvantageous since the natural gas liquids are more profitably employed in uses other than as fuel to which the methane is put. Thus it would be desirable to recover more natural gas liquids separate from methane than is possible by conventional nitrogen rejection processes.

Another problem with such conventional processes is that the use of methane as the heat pump fluid for the cryogenic nitrogen-methane separation column requires either the column operate at a relatively high pressure or else requires the heat pump circuit to operate at vacuum conditions on its low pressure side. Vacuum conditions in the methane circuit are undesirable first because a vacuum is inherently an unsafe operating condition because of possible air infiltration into the circuit, and second because vacuum conditions cause relatively high power inputs because the pumping energies required are substantial. However operation of the nitrogen-methane cryogenic distillation column at high pressure to avoid heat pump circuit vacuum conditions is disadvantageous because the higher pressure puts an operating penalty on the column in the form of increased separation stages, increased reflux liquid requirements, or some combination of the two. It would therefore be desirable to operate the nitrogen-methane distillation column at a lower pressure without requiring the heat pump circuit to operate under vacuum conditions.

It is therefore an object of this invention to provide an improved process for removing nitrogen from natural gases.

It is another object of this invention to provide an improved process for removing nitrogen from natural gases wherein a greater amount of natural gas liquids are recovered separate from methane than is possible by conventional nitrogen rejection processes.

It is a further object of this invention to provide an improved process for removing nitrogen from natural gas wherein a nitrogen-methane cryogenic separation column is operated at lower than conventional pressures while avoiding the need to operate a heat pump under vacuum conditions.

SUMMARY OF THE INVENTION

The above and other objects which will become apparent to one skilled in the art upon a reading of the disclosure are attained by the process of this invention one aspect of which is:

In a process for removing nitrogen from natural gases wherein a nitrogen-containing hydrocarbon stream is first separated into a liquid, containing primarily hydrocarbons having two or more carbon atoms, and into a vapor containing primarily nitrogen and methane, and wherein the vapor stream is further separated in one or more rectification columns into nitrogen and methane, the improvement comprising:

(A) cooling the vapor after the first separation by at least 10° K. to partially condense it;

(B) introducing the condensed portion into a stripping column where it is separated into a liquid, containing primarily hydrocarbons having two or more carbon atoms, and into a vapor containing primarily methane;

(C) recovering the hydrocarbon liquid and the methane vapor of step (B); and (D) introducing the uncondensed portion into the rectification column(s) to be separated into nitrogen and methane.

Another aspect of the process of this invention is:

A cryogenic rectification process for the separation of nitrogen from natural gas comprising:

(a) introducing a nitrogen-containing natural gas feed into a rectification column operating at a pressure in the range of from 200 to 450 psia;

(b) separating the feed in said column into a nitrogen-rich top vapor and a methane-rich bottom liquid;

(c) cooling the top vapor by indirect heat exchange with vaporizing heat pump fluid comprising from 0.5 to 60 mole percent nitrogen and 99.5 to 40 mole percent methane, to partially condense said top vapor;

(d) returning the condensed portion of the top vapor to the column as liquid reflux and removing from the process the uncondensed portion of the top vapor as nitrogen;

(e) warming the bottom liquid by indirect heat exchange with condensing said heat pump fluid to partially vaporize said bottom liquid; and (f) returning the vaporized portion of the bottom liquid to the column as vapor reflux and recovering the unvaporized portion as product natural gas;

wherein said heat pump fluid is at all times at or greater than ambient pressure.

The term "column" is used herein to mean a distillation or fractionation column, i.e., a contacting column or zone wherein liquid and vapor phases are countercurrently contacted to effect separation of a fluid mixture, as for example, by contacting of the vapor and liquid phases on a series of vertically spaced trays or plates mounted within the column or alternatively, on packing elements with which the column is filled. For an expanded discussion of fractionation columns see the Chemical Engineer's Handbook, Fifth Edition, edited by R. H. Perry and C. H. Chilton, McGraw-Hill Book Company, New York Section 13, "Distillation" B. D. Smith et al, page 13–3, *The Continuous Distillation Process*.

The term "stripping column" is used herein to mean a column where the liquid feed is introduced to the top of the column and thereby the more volatile components are removed or stripped from the descending liquid by the rising vapor stream.

The terms "natural gas" and "natural gases" are used herein to mean a methane-containing fluid such as is generally recovered from natural gas wells or petroleum reservoirs.

The terms "nitrogen-containing natural gas stream" and "nitrogen-containing hydrocarbon stream" are used herein to mean a stream having a nitrogen concentration of from 1 to 99 percent.

The terms "natural gas liquids" and "higher hydrocarbons" are used herein to mean hydrocarbons having two or more carbon atoms.

The term "ambient pressure" is used therein to mean the pressure on the outside of the heat pump circuit piping. Generally the ambient pressure is atmospheric pressure.

BRIEF DESCRIPTION OF THE DRAWING

FIG. 1 is a flow diagram of one preferred embodiment of the process of this invention.

DETAILED DESCRIPTION

The invention will be described in detail with reference to the drawing. Referring now to FIG. 1, stream 12 is a gaseous stream from a first separation of a feed from a well or reservoir. The original feed contained nitrogen, methane and higher hydrocarbons and in the first separation the bulk of the higher hydrocarbons were separated out in a liquid. Gaseous stream 12 is the other portion from th first separation and contains nitrogen, methane and some higher hydrocarbons. Typically the nitrogen concentration of stream 12 is from 3 to 90 percent, the methane concentration is from 10 to 97 percent, the higher hydrocarbon concentration is from 1 to 15 percent, and the temperature of stream 12 is from 140° to 230° K.

Stream 12 is cooled in heat exchanger 40 against return streams by at least 10° K., preferably at least 20° K., most preferably at least 30° K., so as to produce partially condensed stream 60 which is introduced into phase separator 42. The vapor portion 61 from phase separator 42 containing substantially nitrogen and methane is further cooled against return streams in heat exchanger 41, expanded through valve 64, and introduced as feed 65 into rectification column 45 operating at a pressure of from 200 to 450 psia. The liquid portion 62 from phase separator 42 containing substantially methane and higher hydrocarbons is expanded through valve 63 and introduced into stripping column 43 at the top of the column. Preferably the liquid portion 62 is expanded to a pressure at least 50 psia lower through valve 63. In other words, stripping column 43 preferably operates at a pressure at least 50 psia lower than the pressure of gaseous stream 12 from the first separation.

In stripping column 43 the liquid falls against rising vapor generated from reboiled liquid at the bottom of the column. The column bottom liquid is reboiled in bottom reboiler 44 which may obtain heat from any convenient source such as heat exchanger 40. The falling liquid and rising vapor countercurrently contact to separate the incoming liquid into a vapor which is removed from the column as stream 66 containing primarily methane, and into a liquid which is removed from the column as stream 11 containing primarily higher hydrocarbons. As shown in FIG. 1, stream 66 may be warmed in heat exchanger 40 and exit as stream 17.

Thus by the use of the phase separation and the further separation of the liquid stream from the phase separation in a stripping column, one is now able to recover additional higher hydrocarbons, shown in FIG. 1 as stream 11 separate from the methane. Without the use of the phase separation and stripping column separation these additional higher hydrocarbons would be recovered as a component of the methane recovery from column 45. Recovery of these higher hydrocarbons separate from the methane is advantageous because the higher hydrocarbons have a greater economic value as chemicals or chemical feedstocks than as fuel and recovery of the higher hydrocarbons with the methane would necessitate their use as fuel rather than in more profitable uses.

Although normally the secondary demthanizer would be utilized to increase the recovery of natural gas liquids, for some applications it may be more advantageous to use the dual demethanizer arrangement to reduce process power requirements. For example, process calculations have indicated that process power savings of several percent can be realized by the dual demethanizer arrangement for equivalent natural gas liquid recovery.

In rectification column 45 the nitrogen-containing natural gas feed is separated into a nitrogen rich top vapor and a methane-rich bottom liquid. The bottom liquid is withdrawn from column 45 as stream 79, and warmed in heat exchanger 51 by indirect heat exchange with condensing heat pump fluid to produce partially vaporized stream 80 which is introduced into phase separator 52. The vapor portion 81 from phase separator 52 is returned to column 45 as reflux vapor. The liquid portion 95 from phase separator 52 is expanded through valve 56 and the liquid stream 67 is warmed in heat exchanger 41 to condition 68, further warmed in heat exchanger 40 and exits as methane product as stream 20. The top vapor is withdrawn from column 45 as stream 70 and cooled in heat exchanger 49 by indirect heat exchange with vaporizing heat pump fluid to produce partially condensed stream 71 which is introduced into phase separator 53. The liquid portion 72 from phase separator 53 is returned to column 45 as reflux liquid. The vapor portion 73 from phase separator 53 is warmed in heat exchanger 47 to condition 74, further warmed in heat exchanger 47 to condition 75, still further warmed in heat exchanger 41 to condition 76 and then warmed in heat exchanger 40 from which it emerges as nitrogen stream 23. This stream may be released to the atmosphere or preferably recovered and further used such as for injection in a well or reservoir for EGR or EOR operations.

Column 45 is driven by a heat pump circuit which takes heat out from the top of the column and pumps it to the bottom of the column. Preferably the heat pump also removes some heat from an intermediate point in the column. The heat pump circuit is closed loop and mass independent from column 45. The heat pump circuit employs a heat pump fluid which is a mixture of nitrogen and methane. The mixture comprises from 0.5 to 60 mole percent nitrogen and from 99.5 to 40 mole percent methane, preferably from 1 to 30 mole percent nitrogen and from 99 to 70 mole percent methane, most preferably from 5 to 20 mole percent nitrogen and from 95 to 80 mole percent methane.

The embodiment illustrated in FIG. 1 employs a two stage or dual pressure heat pump circuit which is a preferred embodiment and will now be described in detail. Heat pump fluid at pressure and at ambient temperature at 89 is cooled in heat exchanger 46 against warming recirculating heat pump fluid to cooled pressurized condition 90. The cooled pressurized heat pump fluid is then condensed in heat exchanger 51 to partially vaporize the bottom liquid from column 45. The condensed heat pump fluid 91 is then subcooled in heat exchanger 47 against warming recirculating heat pump fluid and, most preferably, the warming nitrogen return stream.

The subcooled heat pump fluid emerging from heat exchanger 47 is then divided into two portions. The first portion 92 is further subcooled in heat exchanger 48 against warming recirculating heat pump fluid and, most preferably, the warming nitrogen return stream. The further subcooled heat pump fluid first portion emerging from heat exchanger 48 is expanded through valve 54 to a pressure at least equal to the ambient pressure as stream 97 and passed through heat exchanger 49 to partially condense to top vapor from column 45. The heat pump fluid first portion exits heat exchanger 49 as stream 83, is warmed by passage through heat exchanger 48 to condition 83, further warmed in heat exchanger 47 to condition 84, still further warmed in heat exchanger 46 to condition 85 and passed through compressor 57 where it is compressed to an intermediate pressure. The second portion of the subcooled heat pump fluid is expanded through valve 55 to an intermediate pressure, greater than the pressure to which the first portion is expanded, as stream 96 and passed through heat exchanger 50 where it is warmed to at least partially condense stream 77 which is a vapor stream taken from an intermediate point in column 45. The at least partially condensed stream 78 is then returned to column 45 as additional reflux. The heat pump fluid second portion exits heat exchanger 50 as stream 86, is warmed by passage through heat exchanger 47 to condition 87, further warmed in heat exchanger 46 to condition 88 and combined with the first portion at the intermediate pressure. The combined stream then is passed through compressor 58 where it is compressed and from which it emerges as stream 89 to begin the recirculation anew. It is thus seen that the pressure within the heat pump circuit always equals or exceeds the ambient pressure. Thus vacuum conditions within the circuit are avoided and there is no air infiltration into the circuit.

The use of the mixed heat pump fluid of this invention results in a number of advantages. The use of the defined amount of nitrogen in the heat pump fluid lowers the boiling point of the heat pump fluid and thereby allows separation column 45 to operate at a lower pressure. Operation of the separation column 45 at a lower pressure lowers the condensing temperature of column overhead stream 70. Correspondingly the boiling temperature of the heat pump fluid in heat exchanger 49 must also decrease. The use of the defined amount of nitrogen in the heat pump fluid lowers the boiling temperature of the fluid while maintaining positive pressure at that point in the heat pump circuit, thereby avoiding vacuum conditions in the heat pump circuit.

Lower pressure operation of column 45 allows more effective separation of the feed stream into its nitrogen and methane components by reduction of either the required separation stages or required reflux liquid or some combination of these two factors. Furthermore column 45 may be operated at a lower pressure than in conventional nitrogen-methane single column separation processes without the significant disadvantages which result from vacuum conditions in the heat pump circuit. The single column nitrogen-methane separation process of this invention allows the column to operate at a lower pressure than would be required by a conventional single column while keeping positive pressure at all points within the heat pump circuit. The pressure reduction will depend on the amount of nitrogen in the heat pump fluid and can range up to about 150 psi. For those situations where the nitrogen stream is not intended for re-use in a nitrogen re-injection operation, the released nitrogen at the lower pressure does not waste pressure energy from the process.

Another advantage of the mixed fluid heat pump loop of this invention has to do with the temperature patterns in condenser reboiler 51 and reflux condensers 50 and 49. For those situations where the separation in column 45 does not require high purity products, the top vapor 70 will condense over a temperature range rather than at a constant temperature and the bottom liquid 79 will vaporize over some temperature range rather than at a constant temperature. Similarly the vapor from the column midpoint, which is always a mixture, will condense over a temperature range. Accordingly, if the heat pump fluid is a mixture such that it condenses over a temperature range and vaporizes over a temperature range rather than at constant temperatures, the use of countercurrent heat exchange in reboiler 51 and reflux condensers 50 and 49 will allow better matching of the temperature patterns in those heat exchangers so that the pressure levels in the heat pump loop are reduced. This results directly in lower energy costs associated with the heat pump circuit, that is, lower energy requirements to supply a given amount of reflux liquid for the column separation. The degree of power reduction can be appreciated by considering that for an application where the nitrogen column overhead can contain five mole percent methane, the use of a mixed nitrogen-methane heat pump fluid of about 5 mole percent nitrogen and 95 mole percent methane can reduce the power requirement by about four percent compared to the power requirement when 100 percent methane is the heat pump fluid.

Table I list typical process conditions obtain by a computer simulation of the process of this invention. The stream numbers correspond to those of FIG. 1 and the designation $C_2+$ denotes hydrocarbons having two or more carbon atoms.

TABLE I

| Stream No. | Flow (lb-moles/hr) | Pressure (psia) | Temp. (°K.) | Composition/(mole Percent) $N_2$ | $CH_4$ | $C_2+$ |
|---|---|---|---|---|---|---|
| 12 | 5000 | 400 | 186.9 | 24.1 | 72.5 | 3.4 |
| 60 | 5000 | 400 | 174.6 | 24.1 | 72.5 | 3.4 |
| 61 | 4600 | 400 | 174.6 | 25.6 | 72.7 | 1.3 |
| 62 | 400 | 400 | 174.6 | 5.7 | 70.4 | 23.9 |
| 66 | 275 | 135 | 153.7 | 8.2 | 91.0 | 0.8 |
| 17 | 275 | 135 | 181.7 | 8.2 | 91.0 | 0.8 |
| 11 | 125 | 135 | 183.3 | — | 25.0 | 75.0 |
| 20 | 3693 | 231 | 181.7 | 7.5 | 90.4 | 2.1 |
| 23 | 907 | 400 | 181.7 | 99.5 | 0.5 | — |
| 65 | 4600 | 400 | 156.2 | 25.6 | 72.7 | 1.7 |
| 70 | 3756 | 400 | 122.2 | 99.1 | 0.9 | — |
| 71 | 3756 | 400 | 122.0 | 99.1 | 0.9 | — |
| 72 | 2849 | 400 | 122.0 | 99.0 | 1.0 | — |
| 73 | 907 | 400 | 122.0 | 99.5 | 0.5 | — |
| 77 | 2650 | 400 | 152.6 | 52.5 | 47.5 | — |
| 78 | 2650 | 400 | 148.7 | 52.5 | 47.5 | — |
| 79 | 5176 | 400 | 162.3 | 11.8 | 86.7 | 1.5 |
| 80 | 5176 | 400 | 167.0 | 11.8 | 86.7 | 1.5 |
| 81 | 1484 | 400 | 167.0 | 22.4 | 77.4 | 0.2 |
| 67 | 3693 | 231 | 154.3 | 7.5 | 90.4 | 2.1 |
| 85 | 873 | 32 | 308.0 | 7.0 | 93.0 | — |
| 88 | 467 | 165 | 308.0 | 7.0 | 93.0 | — |
| 89 | 1340 | 368 | 311.0 | 7.0 | 93.0 | — |
| 90 | 1340 | 368 | 182.0 | 7.0 | 93.0 | — |
| 91 | 1340 | 368 | 164.0 | 7.0 | 93.0 | — |
| 96 | 467 | 165 | 142.0 | 7.0 | 93.0 | — |
| 86 | 467 | 165 | 150.0 | 7.0 | 93.0 | — |
| 97 | 873 | 32 | 115.0 | 7.0 | 93.0 | — |
| 82 | 873 | 32 | 121.0 | 7.0 | 93.0 | — |

By the use of the process of this invention one can more efficiently separate a feed stream containing nitrogen, methane and higher hydrocarbons into these component parts. Although the invention has been described in detail with reference to one particularly preferred embodiment, it is appreciated that there are a number of other embodiments which are within th spirit and scope of the claims.

I claim:

1. In a process for removing nitrogen from natural gases wherein a nitrogen-containing hydrocarbon stream is first separated into a liquid, containing primarily hydrocarbons having two or more carbon atoms, and into a vapor containing primarily nitrogen and methane, and wherein the vapor stream is further separated in one or more rectification columns into nitrogen and methane, the improvement comprising recovering substantially all of the hydrocarbons containing two or more carbon atoms which were present in the nitrogen-containing hydrocarbon stream by the steps of:
   (a) cooling the vapor after the first separation by at least 10° K. to partially condense it;
   (b) introducing the condensed portion into a stripping column where it is separated into a liquid, containing primarily hydrocarbons having two or more carbon atoms, and into a vapor containing primarily methane;
   (c) recovering the hydrocarbon liquid and the methane vapor of step (B); and
   (d) introducing the uncondensed portion into the rectification column(s) to be separated into nitrogen and methane.

2. The process of claim 1 wherein the vapor after the first separation is cooled by at least 20° K.

3. The process of claim 1 wherein the vapor after the first separation is cooled by ay least 30° K.

4. The process of claim 1 wherein the stripping column is operated at a pressure at least 50 psi lower than the pressure of the vapor from the first separation.

5. The process of claim 1 wherein said cooling of step (A) is accomplished at least in part by indirect heat exchange of the vapor after the first separation with the methane vapor from the stripping column.

6. The process of claim 1 comprising maintaining said rectification column(s) at lower than conventional pressures, but precluding vacuum conditions in a heat pump circuit by the steps of:
   (a) introducing said uncondensed portion as a nitrogen-containing natural gas feed into a rectification column operating at a pressure in the range of from 200 to 450 psia;
   (b) separating the feed in said column into a nitrogen-rich top vapor and a methane-rich bottom liquid;
   (c) cooling the top vapor by indirect heat exchange with vaporizing heat pump fluid comprising from 0.5 to 60 mole percent nitrogen and 99.5 to 40 mole percent methane, to partially condense said top vapor;
   (d) returning the condensed portion of the top vapor to the column as liquid reflux and removing from the process the uncondensed portion of the top vapor as nitrogen;
   (e) warming the bottom liquid by indirect heat exchange with condensing said heat pump fluid to partially vaporize said bottom liquid; and
   (f) returning the vaporized portion of the bottom liquid to the column as vapor reflux and recovering the unvaporized portion as product natural gas;
wherein said heat pump fluid is at all times at or greater than ambient pressure.

7. The process of claim 6 wherein said heat pump fluid has a composition of from 1 to 30 mole percent nitrogen and from 99 to 70 mole percent methane.

8. The process of claim 6 wherein said heat pump fluid has a composition of from 5 to 20 mole percent nitrogen and from 95 to 80 mole percent methane.

9. The process of claim 6 wherein said heat pump fluid recirculates in a closed loop comprising:
   (1) cooling the heat pump fluid by indirect heat exchange with the bottom liquid;
   (2) dividing the cooled heat pump fluid into a first portion and a second portion;
   (3) expanding the first portion to a pressure at least equal to ambient pressure and warming the expanded first portion by indirect heat exchange with the top vapor;
   (4) expanding the second portion to an intermediate pressure, greater than the pressure to which the first portion is expanded, and warming the expanded second portion by indirect heat exchange with a vapor stream taken from an intermediate point in the column; and
   (5) compressing the expanded first and second portions to form the heat pump fluid to be cooled in step (1).

10. The process of claim 9 wherein in step (4) the intermediate vapor stream is at least partially condensed and is returned to the column as reflux.

11. The process of claim 9 wherein at least one of the warmed expanded portions are further warmed prior to compression by indirect heat exchange with the heat pump fluid prior to its expansion.

12. The process of claim 9 wherein the heat pump fluid is additionally cooled prior to its expansion by indirect heat exchange with the uncondensed portion of the top vapor prior to its removal from the process.

13. The process of claim 9 wherein the first portion is compressed to said intermediate pressure, combined with the second portion, and the combined stream is compressed to form the heat pump fluid to be cooled in step (1).

* * * * *